United States Patent
Moumene et al.

(10) Patent No.: US 7,125,426 B2
(45) Date of Patent: Oct. 24, 2006

(54) LOCKING CAP ASSEMBLY FOR SPINAL FIXATION INSTRUMENTATION

(75) Inventors: Missoum Moumene, Newton, MA (US); Ian Burgess, Barrington, RI (US); George Joseph Ross, Rehoboth, MA (US); Christopher Sicvol, Boston, MA (US); Frank Bono, Collierville, TN (US)

(73) Assignee: DePuy Spine SARL, Le Locle (CH), .

( * ) Notice: Subject to any disclaimer, the term of this patent is extended or adjusted under 35 U.S.C. 154(b) by 169 days.

(21) Appl. No.: 10/606,200

(22) Filed: Jun. 25, 2003

(65) Prior Publication Data

US 2005/0177154 A1    Aug. 11, 2005

Related U.S. Application Data

(63) Continuation-in-part of application No. 09/667,937, filed on Sep. 22, 2000, now Pat. No. 6,755,829.

(51) Int. Cl.
*A61F 2/30* (2006.01)
*A61B 17/56* (2006.01)

(52) U.S. Cl. .......... 623/23.42; 606/61; 606/72; 606/73

(58) Field of Classification Search .......... 606/61, 606/72, 73; 623/23.42
See application file for complete search history.

(56) References Cited

U.S. PATENT DOCUMENTS

| | | | |
|---|---|---|---|
| 4,887,596 A * | 12/1989 | Sherman ............ 606/61 |
| 4,950,269 A | 8/1990 | Gaines |
| 5,257,993 A | 11/1993 | Asher et al. |
| 5,261,912 A | 11/1993 | Frigg |
| 5,306,275 A | 4/1994 | Bryan |
| 5,346,493 A | 9/1994 | Stahurski et al. |
| 5,443,467 A | 8/1995 | Biedermann et al. |
| 5,498,264 A | 3/1996 | Schlapfer et al. |
| 5,501,684 A | 3/1996 | Schlapfer et al. |
| 5,520,689 A | 5/1996 | Schlapfer et al. |
| 5,534,001 A | 7/1996 | Schlapfer et al. |
| 5,545,165 A | 8/1996 | Biedermann et al. |
| 5,615,965 A | 4/1997 | Saurat et al. |
| 5,672,176 A | 9/1997 | Biedermann et al. |
| 5,716,356 A | 2/1998 | Biedermann et al. |
| 5,725,527 A | 3/1998 | Biedermann et al. |
| 5,741,255 A | 4/1998 | Krag et al. |
| 5,814,046 A | 9/1998 | Hopf |

(Continued)

FOREIGN PATENT DOCUMENTS

DE       94 03 231        4/1994

(Continued)

*Primary Examiner*—Pedro Philogene
(74) *Attorney, Agent, or Firm*—Nutter, McClennen & Fish LLP

(57) ABSTRACT

A spinal anchor assembly for securing a fixation element includes an anchor element and a twist-in cap. The anchor element is configured for attachment to a bone, typically by comprising a mono- or polyaxial screw or hook, and includes a proximal portion having an open slot for receiving the fixation element and having radially inwardly protruding flange segments. The twist-in cap is received in and closes the open slot. The proximal portion of the anchor and the cap are adapted to twist-lock together by a partial rotation of the cap from an open position to a closed position to cover the slot so as to capture the fixation element and to lock the cap in the closed position.

25 Claims, 17 Drawing Sheets

U.S. PATENT DOCUMENTS

| | | |
|---|---|---|
| 5,873,878 A | 2/1999 | Harms et al. |
| 5,961,517 A | 10/1999 | Biedermann et al. |
| 6,077,262 A * | 6/2000 | Schlapfer et al. ............ 606/61 |
| 6,106,526 A | 8/2000 | Harms et al. |
| 6,110,172 A | 8/2000 | Jackson |
| 6,296,642 B1 * | 10/2001 | Morrison et al. ............ 606/61 |
| 6,302,888 B1 | 10/2001 | Mellinger |
| 6,565,565 B1 * | 5/2003 | Yuan et al. .................... 606/61 |
| 6,755,829 B1 * | 6/2004 | Bono et al. ................... 606/61 |
| 2001/0025180 A1 | 9/2001 | Jackson |
| 2002/0120272 A1 | 8/2002 | Yuan et al. |
| 2002/0143332 A1 | 10/2002 | Lin et al. |
| 2004/0030337 A1 | 2/2004 | Alleyne et al. |

FOREIGN PATENT DOCUMENTS

| | | |
|---|---|---|
| JP | 2001-276086 | 10/2001 |
| WO | WO 00/19923 | 4/2000 |

* cited by examiner

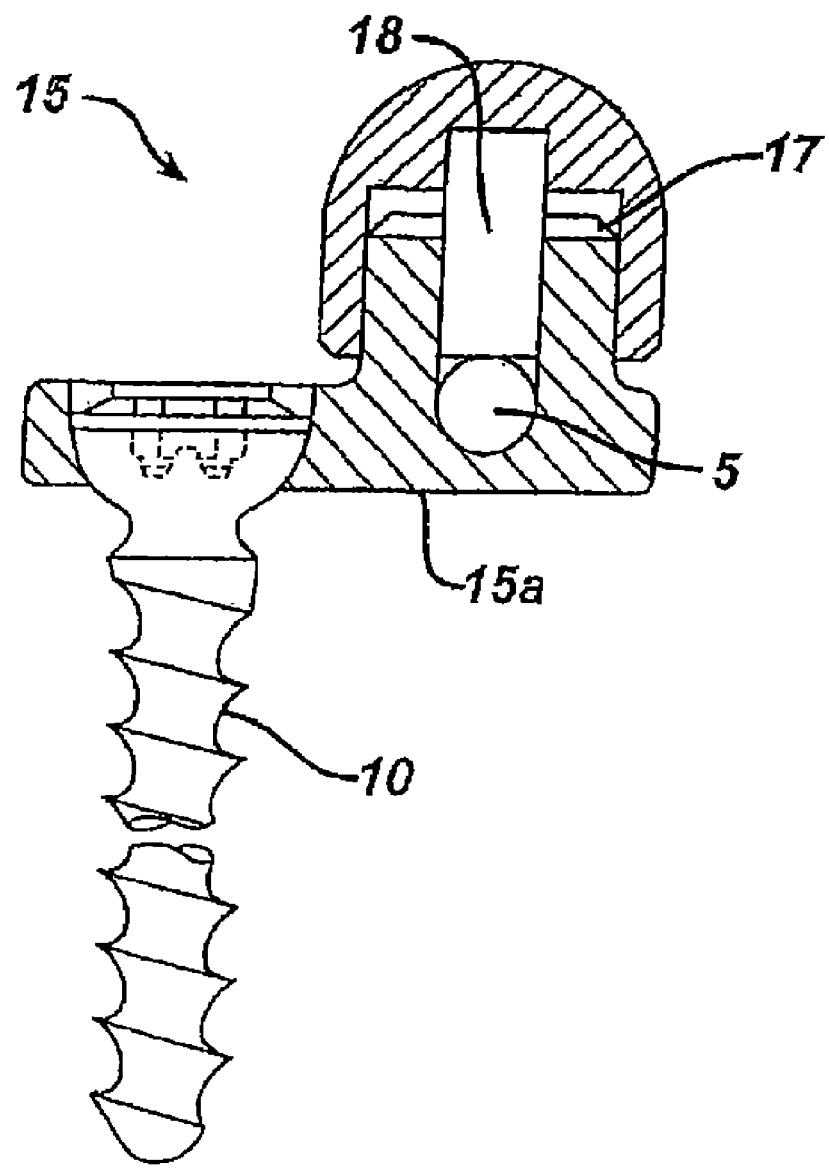

LOCKING CAP ASSEMBLY FOR SPINAL FIXATION INSTRUMENTATION

CROSS REFERENCE TO RELATED APPLICATION

This application is a continuation-in-part of U.S. patent application Ser. No. 09/667,937 to Bono et al., filed on Sep. 22, 2000, and entitled "Lock Cap Anchor Assembly for Orthopaedic Fixation," now issued as U.S. Pat. No. 6,775,829, on Jun. 29, 2004, which application is incorporated herein by reference in its entirety.

BACKGROUND OF THE INVENTION

The use of spinal fixation instrumentation to align and/or fix a desired relationship between adjacent vertebral bodies is well established. Such instrumentation typically includes a spinal fixation element, such as a relatively rigid fixation rod, that is coupled to adjacent vertebrae by attaching the element to pedicle screws which have been inserted into the patient's vertebrae or to spinal hooks which can be placed into a vertebral arch for coupling to the vertebral bodies. Once installed, the spinal fixation instrumentation holds the vertebrae in a desired spatial relationship, either until desired healing or spinal fusion has taken place, or for some longer period of time.

One example of a rod based spinal fixation system is provided in U.S. Pat. No. 5,005,562, issued Apr. 9, 1991 to Cotrel (which is hereby incorporated by reference). This system includes pedicle screws and spinal hook vertebral coupling elements (both screws and hooks) having integral U-shaped bodies that extend outward from the vertebrae to which they are attached. A spinal fixation rod is shaped as desired and fitted into the "U" of U-shaped bodies of adjacent vertebrae. The inner surfaces of the U-shaped body are threaded to accept a set screw, and rod is fixed to the vertebral coupling elements by threading a set screw into each of the U-shaped bodies to lock in the rod.

U.S. Pat. No. 5,545,165, issued Aug. 13, 1996 to Biedermann et al. (and incorporated herein by reference), illustrates an improvement in closure systems for fixing a rod to vertebral coupling elements over those provided by Cotrel. The Biedermann et al. system also uses pedicle screws and spinal hooks having U-shaped bodies that extend outward from the vertebrae to which they are attached. The U-shaped bodies of the Biedermann et al. system are threaded on both the inside and the outside. The rod is therefore locked in by both an inner set screw and an outer lock nut. In the illustrated embodiments, the inner set screw is adapted to be driven on its threads using a hex-shaped driver element, and the outer locking nut is provided with hex-shaped flat outer surfaces suitable for engagement with a wrench or similar driving tool.

U.S. Pat. No. 5,443,467, issued Aug. 22, 1995 to Biedermann et al. (and incorporated herein by reference) illustrates the use of an inner set screw and an outer lock nut to lock a rod into a U-shaped body in a polyaxial screw system. In this system, a pedicle screw having a spherical head is captured within a separate U-shaped receiver body. The angle of the screw with respect to the body can be changed until a head-locking element is tightened to lock the angle of the screw head within the receiver body. According to Biedermann et al., this combination of an inner set screw and an outer locking nut provides an advantage in that the force acting on the rod can be independently adjusted by either the inner set screw or the outer locking nut—a particularly useful advantage where the rod being fastened is curved and an exact fastening might only be possible by independent adjustment of the two closure elements. In addition, when tightened, the inner set screw and the outer locking nut tend to lock each other in their tightened positions.

Another style of closure system utilizes a cap element with a dovetail or dovetail channel that slides over the rod to close the top of the slot and wedge the rod firmly in position. This latter construction involves no rotation of threaded members, but has the disadvantage that a certain amount of unobstructed lateral space along the rod adjacent to the connection point is necessary for the sliding installation of the closure cap. Furthermore, the cap inserts or sliding wedge closures, while they eliminate the need for awkward screwing or rotational motion during installation, cannot be used with some existing reduction screws, translation hooks or other common hardware having lengthy protruding guide members, reduction tabs or the like. Moreover, the wedge/cap closures are a specialized component that may require the user to switch entirely over to a proprietary line of orthopaedic hardware if he is to utilize the full range of hook, tab, plate and screw fixation points that may be required in spinal surgery.

While the closure systems described above have in at least some instances been quite successful, it would be beneficial to provide a closure assembly that could securely lock down a rod down while requiring only a small number of locking steps by the surgeon and small lateral clearances surrounding the closure.

SUMMARY OF THE INVENTION

The present invention improves on the art by providing a spinal anchor assembly for securing a fixation element having an anchor element and a twist-in cap. The anchor element is configured for attachment to a bone, typically by comprising a mono- or polyaxial screw or hook, and includes a proximal portion having an open slot for receiving the fixation element and having radially inwardly protruding flange segments. The twist-in cap is received in and closes the open slot. The proximal portion of the anchor and the cap are adapted to twist-lock together by a partial rotation of the cap from an open position to a closed position to cover the slot so as to capture the fixation element and to lock the cap in the closed position.

In specific embodiments, the cap and anchor elements each include detent elements that engage to lock the cap in the closed position. A first one of the cap and anchor detent elements can be a protrusion, while a second one of the cap and anchor detent elements can be a recess configured to capture the protrusion and the anchor detent element can be provided on an anchor flange segment. Still further, the first one of the cap and anchor detent elements can be a longitudinal protrusion and the second one of the cap and anchor detent elements can be a longitudinal slot.

In further specific embodiments, the cap includes radially outwardly protruding flange segments with the cap flange segments being captured by the anchor element flange segments when the cap is in the closed position. The cap and anchor flange segments can be provided with a radial slant in a direction that extends toward a distal end of the anchor element when moving inward toward the cap and this radial slant can be configured such that securing the fixation element within the slot causes the flange segments to slide with respect to each other, causes a displacement of the anchor flange segments inwardly, and/or causes any detent elements to engage with greater strength. Pressure can be provided to further secure the fixation element in the open slot by providing the cap with a centrally placed clamping member that may be tightened down on the fixation element. In specific embodiments, the clamping member may be a set screw threaded into a central bore in the cap.

In an additional aspect of the invention, an anchor assembly for securing a fixation element is provided having an anchor element and a closure element. The anchor element is adapted for attachment to bone and defines a central longitudinal axis. The anchor element has an open slot for receiving the fixation element, side walls on opposed sides of the open slot, a proximal portion, a distal portion, and an anchor flange segment extending from each of the side walls in a direction toward the central longitudinal axis. The anchor flange segments each include an inferior contact surface. The closure element closes the open slot in the anchor element and applies pressure to the fixation element to capture the fixation element within the open slot. The closure element includes a closure body and a plurality of closure flange segments extending from the closure body in a direction that is transverse to the anchor element central longitudinal axis when the closure element is placed in the open slot. Each closure flange segment includes a superior contact surface extending in a direction away from the central longitudinal axis when the closure element is placed in the open slot so that the closure flange segment superior surfaces engage the anchor element flange segment inferior surfaces over a contact area when the closure element is placed in a closed position in the anchor element open slot. The closure flange segments further include exterior surfaces that extend away from the longitudinal axis and proximally when the closure element is placed in the open slot to provide a partial cone shaped outer surface to the closure flanges.

In a still further aspect of the invention, an anchor assembly for securing a fixation element is provided having an anchor element and a closure element. The anchor element is adapted for attachment to bone and defines a central longitudinal axis. The anchor element has an open slot for receiving the fixation element, side walls on opposed sides of the open slot, a proximal portion, a distal portion, and an anchor flange segment extending from each of the side walls in a direction toward the central longitudinal axis. The anchor flange segments each include an inferior contact surface extending in a direction toward the central longitudinal axis and toward the distal portion to define a radial slant. The closure element closes the open slot in the anchor element and applies pressure to the fixation element to capture the fixation element within the open slot. The closure element includes a closure body and a plurality of closure flange segments extending from the closure body in a direction that is transverse to the anchor element central longitudinal axis when the closure element is placed in the open slot. Each closure flange segment includes a superior contact surface extending in a direction away from the central longitudinal axis and toward the proximal portion of the anchor element at the radial slant when the closure element is placed in the open slot so that the closure flange segment superior surfaces engage the anchor element flange segment inferior surfaces over a contact area when the closure element is placed in a closed position in the anchor element open slot. The radial slant is further configured to permit the sliding of the anchor flange segment inferior surfaces with respect to the closure flange segment superior surfaces upon pressure being applied on the fixation element.

BRIEF DESCRIPTION OF THE DRAWINGS

The invention will be more fully understood from the following detailed description taken in conjunction with the accompanying drawings:

FIGS. 1A–1C schematically illustrate various spinal fixation rod anchor assemblies of the prior art;

DETAILED DESCRIPTION OF THE INVENTION

The invention and its range of embodiments will be better understood following a brief description of prior art, illustrating approaches to one- and two-part anchor assemblies, as well as certain common constructions.

Figure 1A:
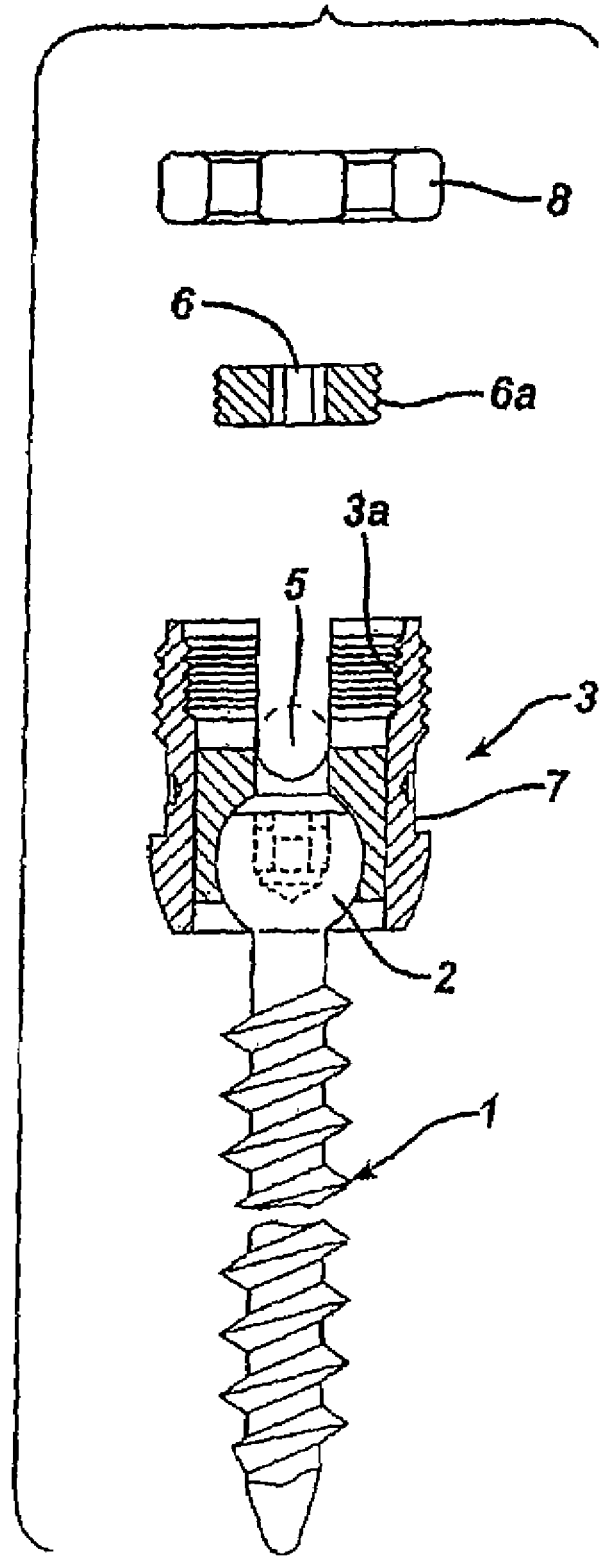
Figure 1C:
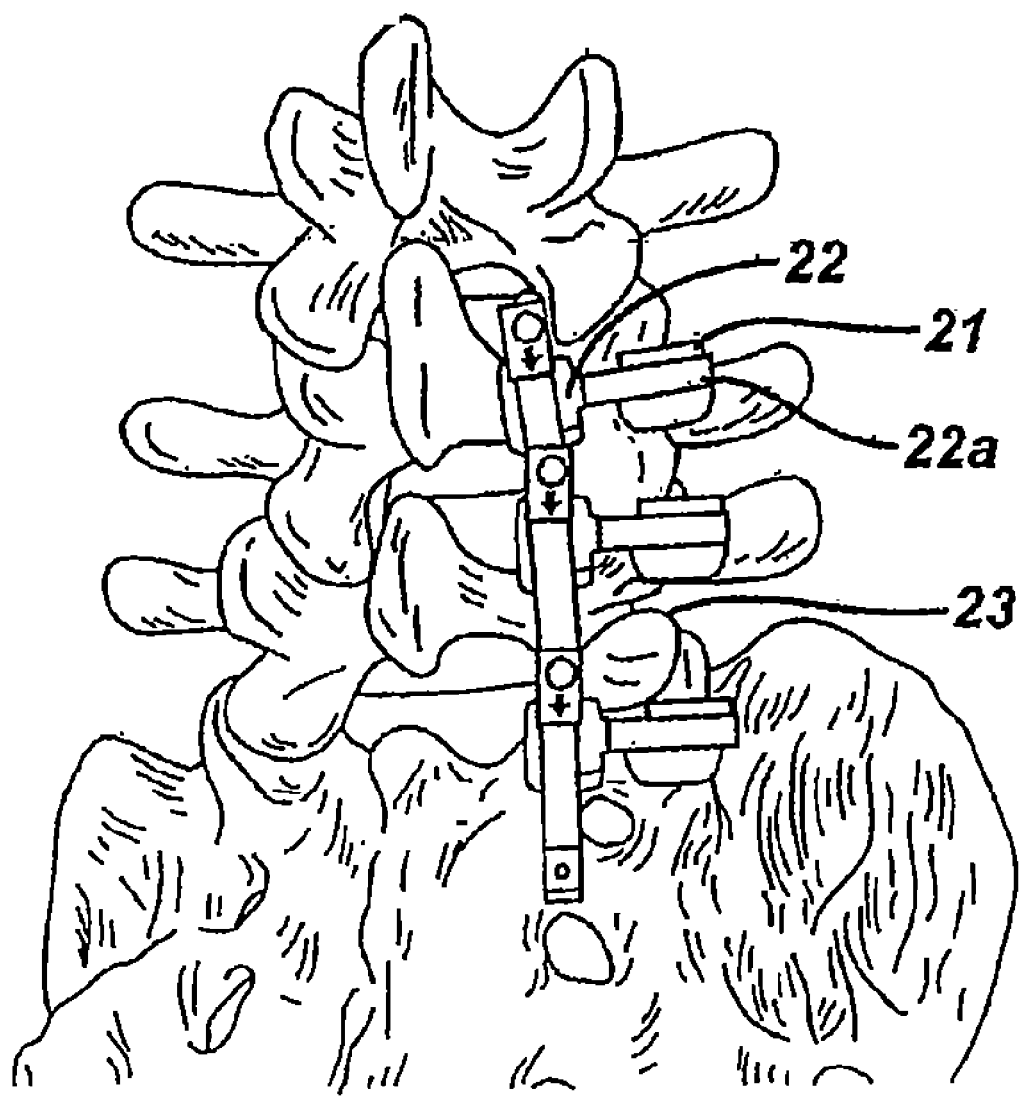

FIGS. 1A–1C illustrate prior art anchor mechanisms for securing a fixation rod as used in spinal fixation. FIG. 1A illustrates an anchor screw, while FIG. 1B shows an offset tab having a slotted post for receiving the rod and FIG. 1C shows a combined system in which anchor screws secure rod-shaped offset elements that, in turn, each terminate in an end that grips a common fixation rod. In the anchor screw of FIG. 1A, a screw 1 with a rounded head 2 carries a slotted top member 3 into which a rod 5 shown in phantom is clamped by screwing down a threaded press ring or set screw 6. The press ring 6 is turned by engagement along its central portion e.g., by an Allen wrench, and has external threads 6a which fit corresponding internal threads 3a of the top member 3. A separate body 7 fills the space between the inner wall of the top 3 and the ball head 2 of the screw 1, so that when the rod is pressed down by the member 6, the screw head is firmly gripped and all parts are rigidly held together. An external nut 8 threads over the outside of the top to further strengthen and lock the assembly. For this prior art anchor member, the screw 1, the press member 6 and the nut 8 may all be installed with a straight tool, such as an Allen wrench or socket wrench, inserted directly along the axis of the screw.

FIG. 1B shows another anchor assembly 15 for receiving a fixation rod 5. In this assembly, an offset tab construction having a body 15a that is anchored by a conventional bone screw 10 and including a slotted post (not numbered) for receiving the rod, is closed by a cap nut 17 which carries a pressure member 18 centrally thereon to press down against the rod 5 as the nut is tightened. In each of these two constructions, the member 6 or 17 for clamping down against the rod 5 installs by rotational movement.

Another prior art anchor assembly is illustrated in FIG. 1C. In this article, a slotted body 21 or 22 is carried either on a bone screw (not visible in the Figure) or on a short length of offset rod 22a. In both cases, the slotted body 21 or 22 receives a rod and clamps it tightly. In this assembly the slotted head member 21 or 22 has angled or dovetailed walls at its upper portion, and a correspondingly shaped sliding cap member 23 is pressed along the dovetail into the upper region, sliding along the axis of the slot to close the slot and wedge firmly against the rod passing therethrough. As noted above, this construction has a disadvantage that a lateral clearance along the length of the rod is necessary for movement of the closure member 23 into position. Other constructions are shown in U.S. Pat. Nos. 5,346,493, 5,257,993 and elsewhere.

Thus, the art includes both one-piece, and many-piece anchor assemblies, and these may look like screws, or may be specialized elements that are themselves to be anchored by another assembly. As described further below, the present invention provides a closing and fixing mechanism of enhanced utility, with a structure adaptable to much of this broad range of hooks, screws, connector assemblies and other orthopaedic anchor hardware involving one or more rod, cable, wire or other linking elements.

Figure 2:
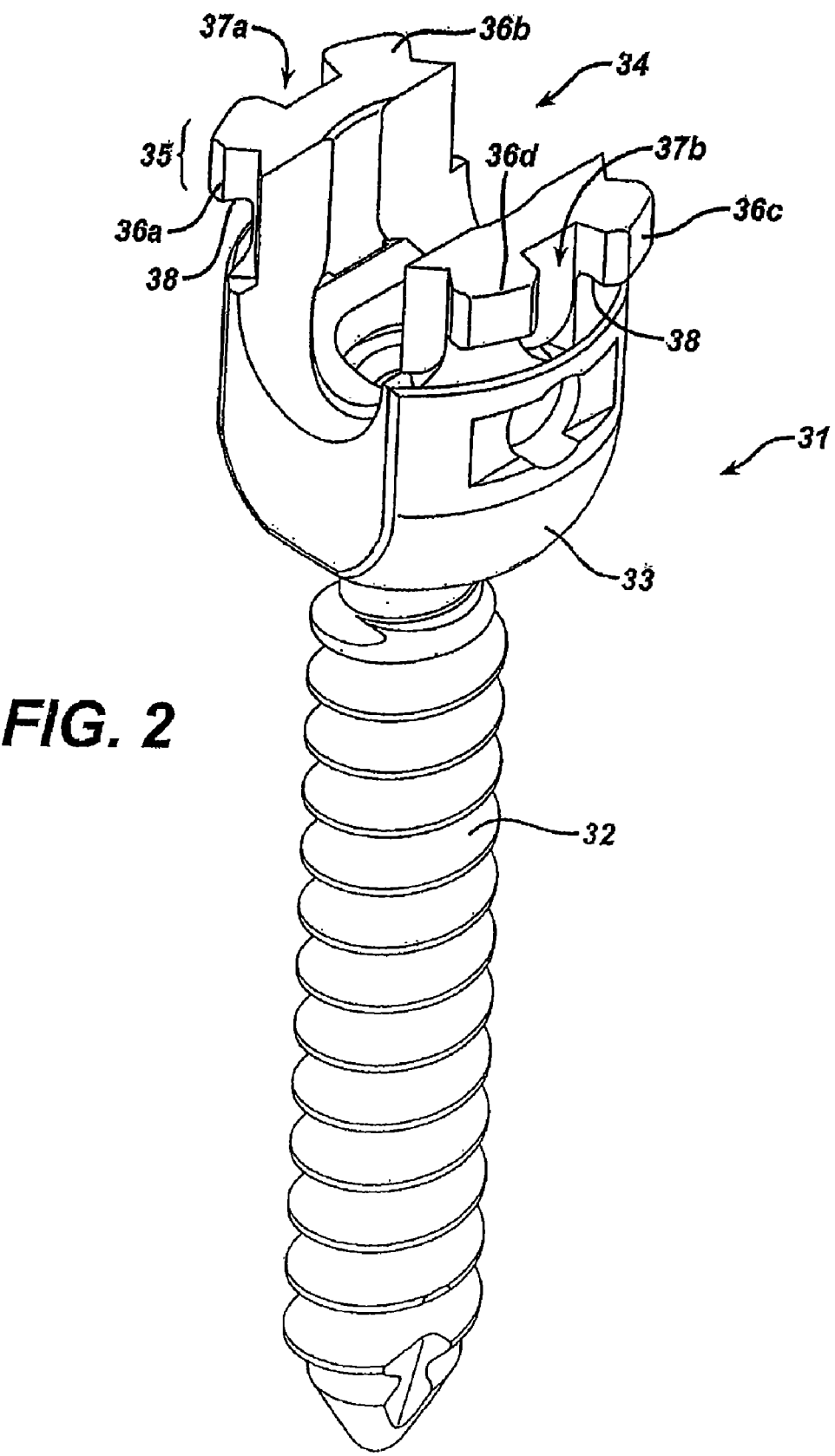
FIG. 2 shows an embodiment of an anchor screw of the present invention.
Figure 3:
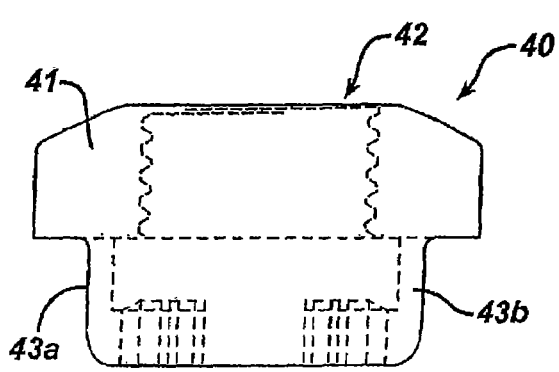
FIGS. 3 and 3A–3C show views of a closure cap utilized with the anchor screw of FIG. 2 in accordance with the present invention.
Figure 3A:
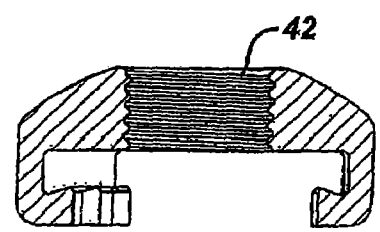
Figure 3B:
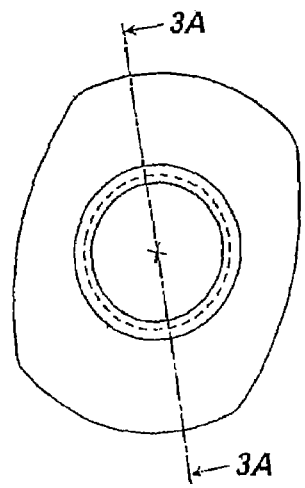
Figure 3C:
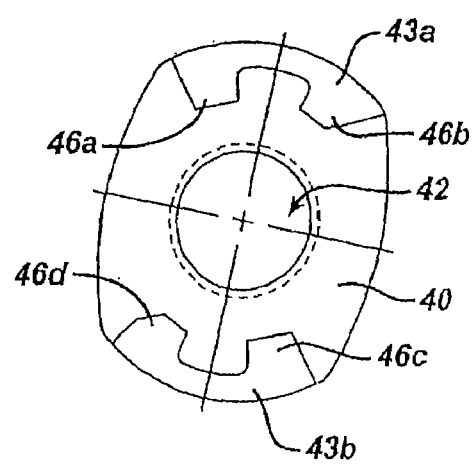

FIG. 2 illustrates a first embodiment of an anchor screw assembly 31 of the present invention. As shown, the anchor screw assembly 31 includes a screw 32 and a top member 33 which may be integral with the screw or, like the prior art construction of FIG. 1A, may be a separate head member that secures to the proximal end of the screw 32. The top member 33 includes a slot indicated generally by 34 for receiving a rod, and contains at its uppermost region 35, a plurality of segmented or partial flange members 36a, 36b, 36c, 36d which extend radially outward from its perimeter and have respective slots or spaces 37a, 37b therebetween. As further shown in FIG. 2, each of the flange segments 36a, 36b, 36c, 36d has a lower surface 38, as best seen in the end views of flange segments 36a and 36c, that engages a closure cap 40 (FIGS. 3A–3C). While not shown, one or more of the flange segments or cap may include a notch, detent or catch or a jamming feature, to prevent rotation in the opposite sense.

The anchor screw or hook 31 of FIG. 2 is used in conjunction with a closure cap 40 which is shown in an upward-facing view, from below, in FIG. 3C. The cap 40 fits over and around the upper portion 35 of the slotted, rod receiving top member. As shown FIG. 3, the cap 40 includes a body 41 having a central threaded bore 42 extending therethrough and a pair of dependent side members 43a, 43b on opposed peripheral sides thereof which extend downward on opposed sides surrounding the outer circumference of the top member 33. Each of the side members 43a, 43b carries mating inwardly directed protrusions 46a, 46b, and 46c, 46d, respectively, which are spaced apart and positioned to correspond to the segmented flange members 36a–36d of the screw head. In particular, the protrusions 46a to 46d are positioned below the main body of the cap 41 by an amount corresponding to the maximum thickness of the flange segments 36a to 36d, and are rotationally offset so as to pass down through the gaps between segments and rotate into gripping engagement around the segments by a partial rotation of the cap 40 about the screw head assembly or top member 33, in the manner of a bayonet mounted lid closure. This secures the cap 40 on the top member closing the slot to prevent movement of the rod or cable from the head along the axial direction of the screw 32. A set screw (not shown) threaded through the aperture 42 is then tightened to clamp firmly down against the rod, cable or other linkage captured in the slot 34 (FIG. 2).

Advantageously, with the foregoing construction, the anchor screw 31 and the closure assembly 40 as well as the set screw (not illustrated) all install by simple rotational movement of a tool that extends directly along the axis of the screw. Moreover, as illustrated, the initial locking of the cap on the head assembly is effected by a small rotational movement, substantially less than one-half turn, which corresponds approximately to the length of the lower surface 38 of one flange segment, or about 20 degrees of rotational movement. Thus a very slight movement is sufficient to capture the rod 5 (FIGS. 1A–1C) within the slot 34 during initial setup or fitting of the fixation rod.

This twist-lock flanged anchoring assembly with a cap structure of the present invention is readily adapted to diverse other fixation screws of known design, and thus in various alternative embodiments and adaptations may carry forward the advantages of those other designs. Thus, for example, the locking cap assembly of FIGS. 2–3 of the invention may be adapted to an anchor assembly such as a reduction screw, anchor screw, or hook in which the anchor member possesses protruding reduction tabs that extend upwardly from the head of the anchoring assembly.

Figure 4:
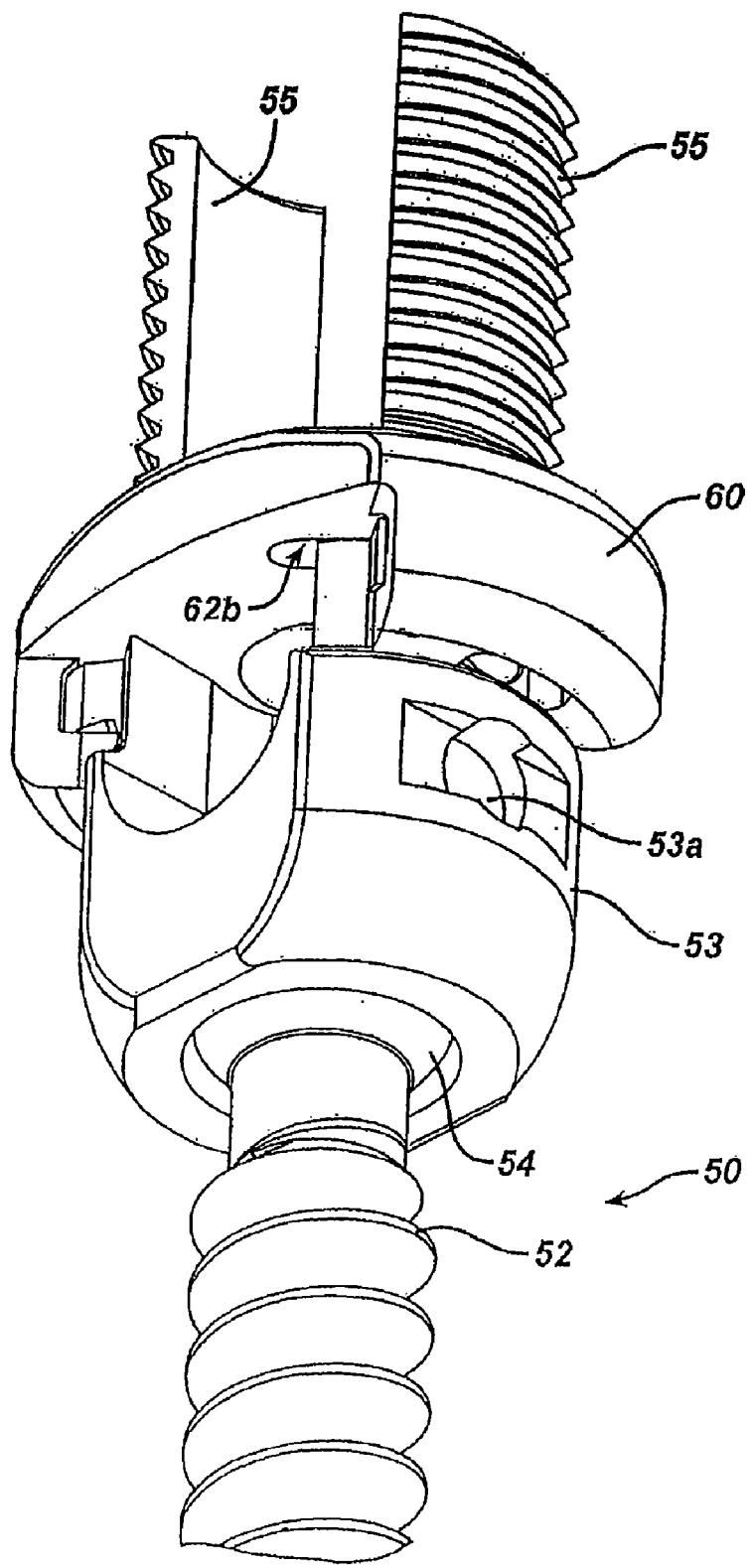
FIG. 4 shows a second embodiment of an anchor member and closure cap of the invention.

Such an embodiment 50 is shown in FIG. 4. In this embodiment, the head 53 of the anchor assembly has a pair of reduction tabs 55 extending upwardly from the sides of the slot. In this case, the invention contemplates a closure cap 60 with a rim-engaging securing structure similar to that of cap 40 for engagement by a small rotational motion, but the cap structure further includes a pair of arcuate slots 62a, 62b located in its central region and sized for passage of the reduction tabs 55 or other protruding head structure therethrough. Each of the slots 62a, 62b extends past the edges of the tabs 55, permitting sufficient rotation of the cap to lock the cap in position. The structure of the cap itself strengthens or supports both the surrounding wall of the rod receiving slot, and the thin-walled tabs 55 which rise therefrom, while leaving the central on-axis region above the cap entirely unobstructed for insertion, for example, of a set screw along an axial direction, and permitting line-of-sight access by a driver for installation.

In any of the foregoing constructions, the rod-receiving head assembly or top member 33, 53 may be integral with the anchor screw 35, 52 or may be constituted by a separate slotted head member that fits about the top of the screw to grip the rod or other connecting linkage. Thus, the invention applies to diverse anchors, hooks, monoaxial screws, transverse connections or tandem connections, slotted connectors or the like.

FIG. 4 illustrates this aspect of the invention for a reduction tab embodiment of which the head is separate from the screw. As shown, the anchor screw assembly 50 has a screw body 52 with an enlarged head 54 which may, for example, have an Allen or other female socket formed therein (not shown) for applying torque along the axis of the screw to insert the screw in bone. A slotted top member 53 having a tapered interior bore is first fitted over the head 54, receiving the screw body from above, capturing the enlarged ball head 54 of the screw therein. A compressed member (not shown) which may be similar to element 7 of FIG. 1A, may be provided to create a binding fit, and this element may be fixed in place, for example, by swaging at opposed surface relief drillings 53*a*, or it may fit by simple compression. The provision of top member 53 as a separate head structure that is loosely fixed to, but originally decoupled from, the screw 52 in this manner allows the slot angle to be set at a later stage of installation, while avoiding the risk of losing separate small components.

Figure 4A:
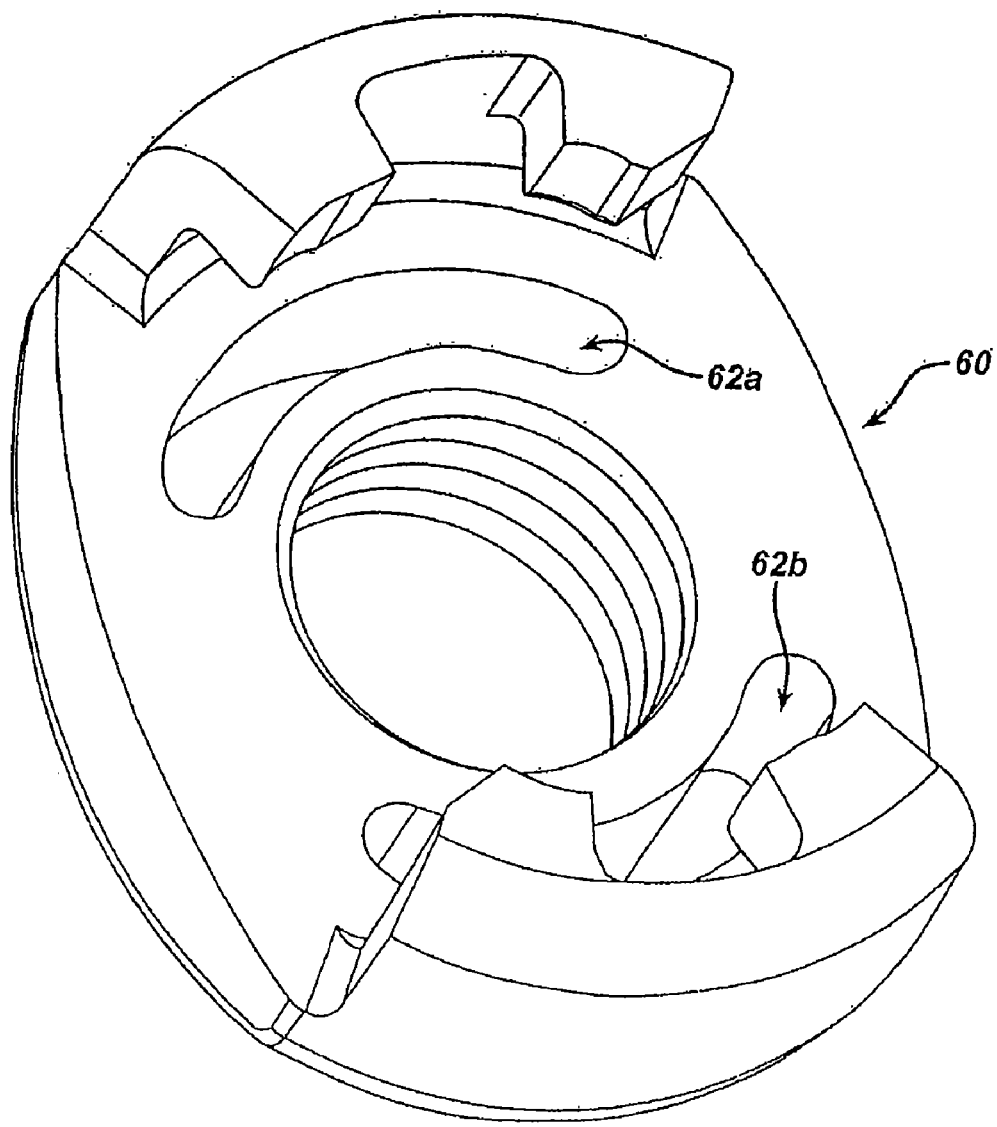
FIG. 4A is a perspective view from below of the cap of FIG. 4.

The cap 60 of this embodiment, which is shown in a perspective view from below in FIG. 4A, is similar to that of the first described embodiment, but includes arcuate slots 62*a*, 62*b* to accommodate the projecting reduction tabs. In each case, the cap member having a dependent locking rim that grips the outside of the slotted top and closes the slot by a partial rotation, provides a simple and unobstructed procedure for closing the head of the anchor and capturing the rod, cable or other linkage in the anchor assembly and clamping the linkage while fixing the orientation.

Figure 4B:
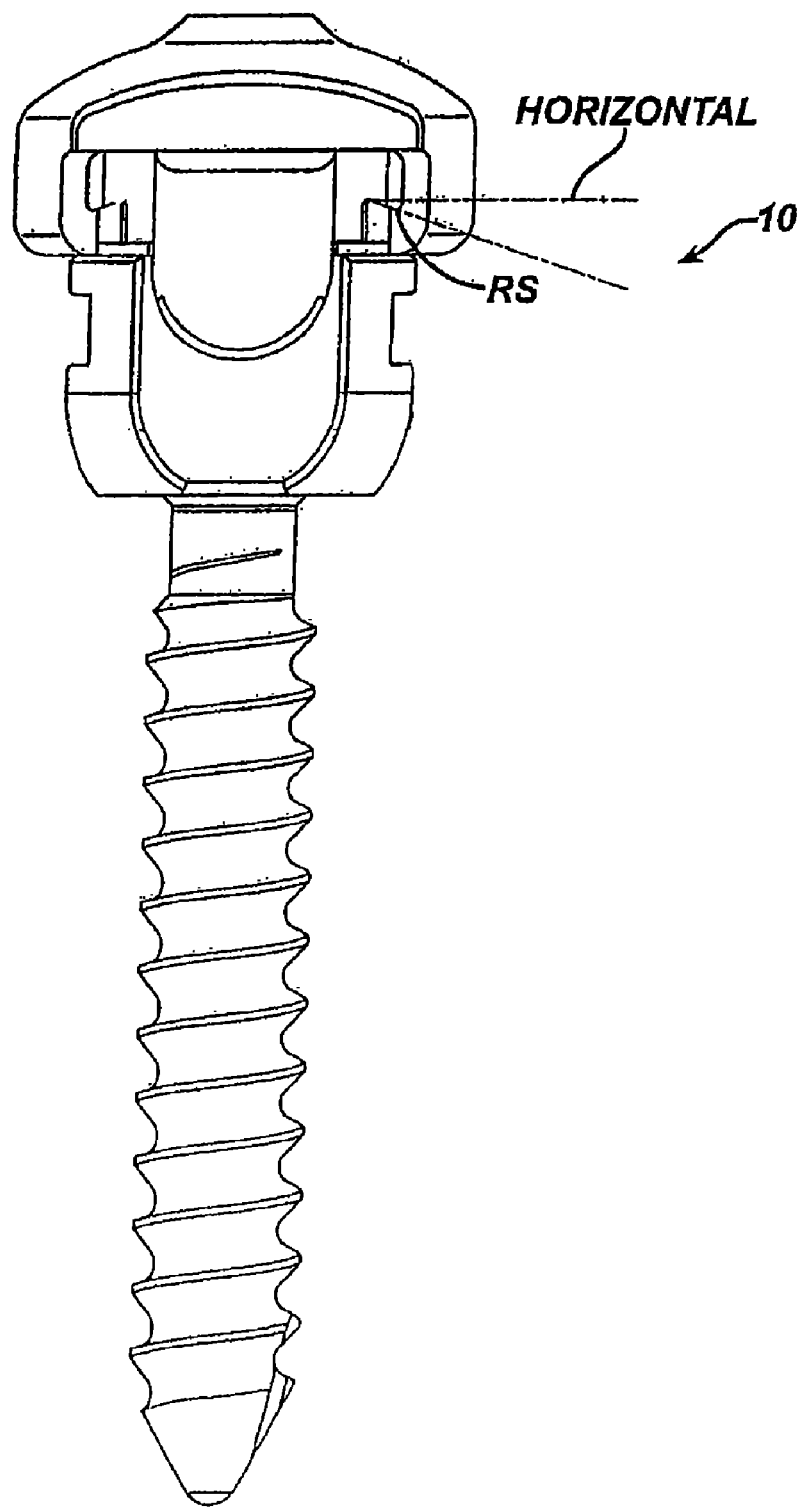
FIG. 4B illustrates details of the anchor member of FIG. 4.

In each of the foregoing illustrated embodiments, the cap extends radially beyond the outer radius of the anchor screw head assembly, and has a rim that extends to a greater diameter, and slides between the segmented flange bosses 36 to rotate into a captured position which closes the slot and captures the rod or other linkage within the head of the anchor assembly. A radial slant "RS" at an angle Θ may be provided on one or more faces of the opposed locking members as shown in the detail FIG. 4B to assure that they cannot slip radially outward under pressure.

In further embodiments, the invention contemplates a twist-on cap member which fits within the head of the anchor assembly rather than extending over and locking on the outside of the head.

Figure 5:
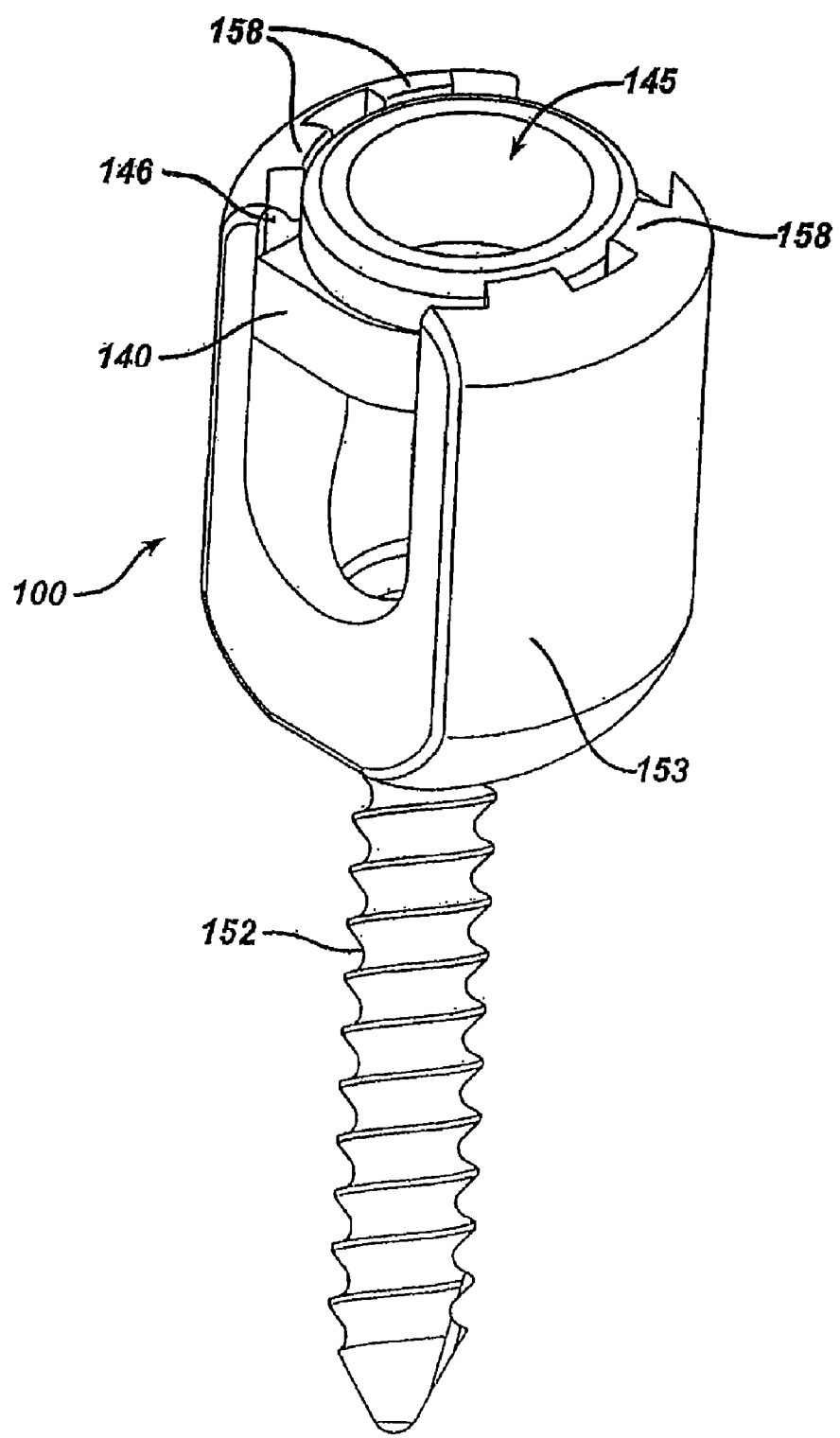
FIG. 5 shows a third embodiment of an anchor member and closure cap of the invention.

FIG. 5 illustrates one embodiment 100 of such a twist-in anchor closing mechanism. As shown, the anchor assembly 100 has a screw portion 152 for anchoring in bone, and a head portion 153 for receiving the rod, cable or other linkage. A closure cap 140 closes the slotted end of head 153. As in the previously described embodiments, the screw and head may be separate assemblies, in which case the upper portion of the screw preferably has a ball end as described above that allows the head to pivot about the axis of the screw and achieve a further degree of freedom in angular orientation before clamping down. As with the earlier described embodiments, the cap or closure portion 140 may have a central bore 145 which is internally threaded to accommodate a set screw to further clamp the rod in the slot; however, to simplify the drawing, threads are omitted from FIG. 5.

The internal closure cap 140 has a plurality of radially protruding flange segments 146, of which one is visible in the Figure, and the cap is pushed downwardly on the head so the respective inward and outward directed segments pass between each other, in a manner similar to the above-described embodiments. Thus, the segments 146 fit between corresponding inwardly protruding segments 158 of the head 153 and lock thereagainst by a small rotation of the cap 140.

Figure 6A:
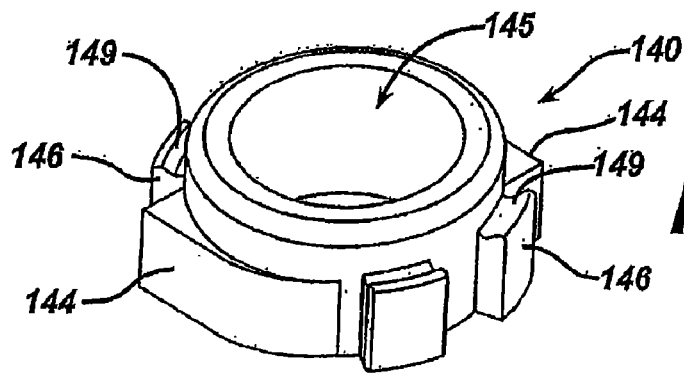
FIGS. 6A, 6B and 6C illustrate the cap and head structure, respectively, of embodiment of FIG. 5 in greater detail.
Figure 6B:
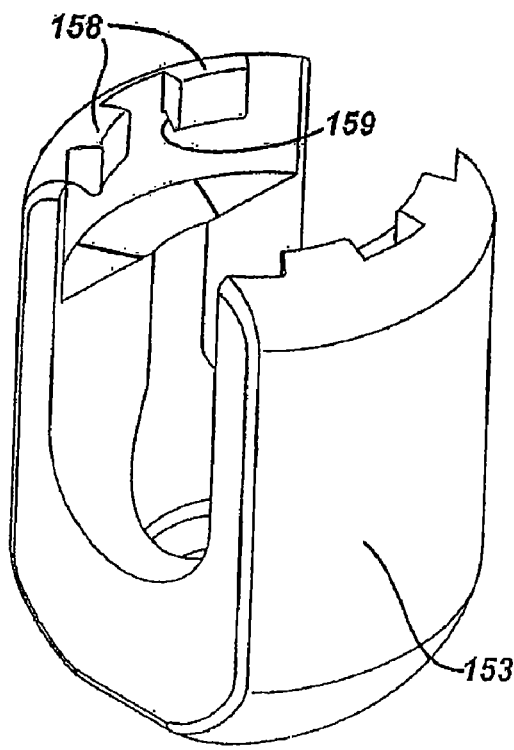

FIGS. 6A and 6B illustrate the structure of the twist-in cap 140 and the slotted head 153 in greater detail.

Figure 6C:
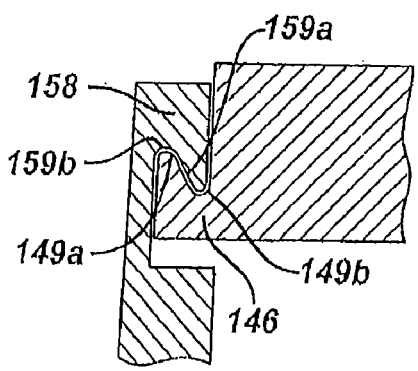

FIG. 6A shows the closure cap 140, and FIG. 6B shows the head assembly 153, of an internal closure locking cap of FIG. 5. As shown, the head assembly 153 of the anchor screw has a plurality of internally projecting bosses 158 and the closure cap 140 has corresponding outwardly projecting bosses 146. Respective bosses 146, 158 are dimensioned such that the cap 140 may be pushed downwardly between spaces of corresponding bosses to position the upper surface 149 of the cap bosses below the lower surface 159 of the retaining head bosses 158. As shown in FIGS. 6A and 6B, these mating contact surfaces are angled or sloped downwardly with a radial slant "RS" at an angle Θ (illustrated in FIGS. 5 and 6B) toward the center. In this way, when the cap 140 is rotated to place opposed bosses in an engagement with each other, the cap exerts a net inwardly directed force on the head to prevent spreading of the retaining slot. This effect can be particularly advantageous when a set screw (not shown) is deployed in bore 145 as is further described below. The contours of the sloped ends are relatively sharply defined, effectively forming a circumferential ridge 149*a*, 159*a* and groove 149*b*, 159*b* on each of the respective components (FIG. 6C). The ridge of one part fits in the groove of the other, so that the closure is centered and grips over a substantial contact area.

As best seen in FIGS. 5 and 6A, the twist-in cap has opposed edge flats 144 which may provide a contact or engagement surface for a tool such as a wrench used for turning the cap upon installation. Each of the flats 144 has a corner to prevent over-rotation of the cap, so that upon insertion it rotates to exactly position the respective bosses 146, 158 opposite each other as the anchor assembly is closed. The set screw is then tightened to secure the fixation linkage captured in the slot.

Figure 7A:
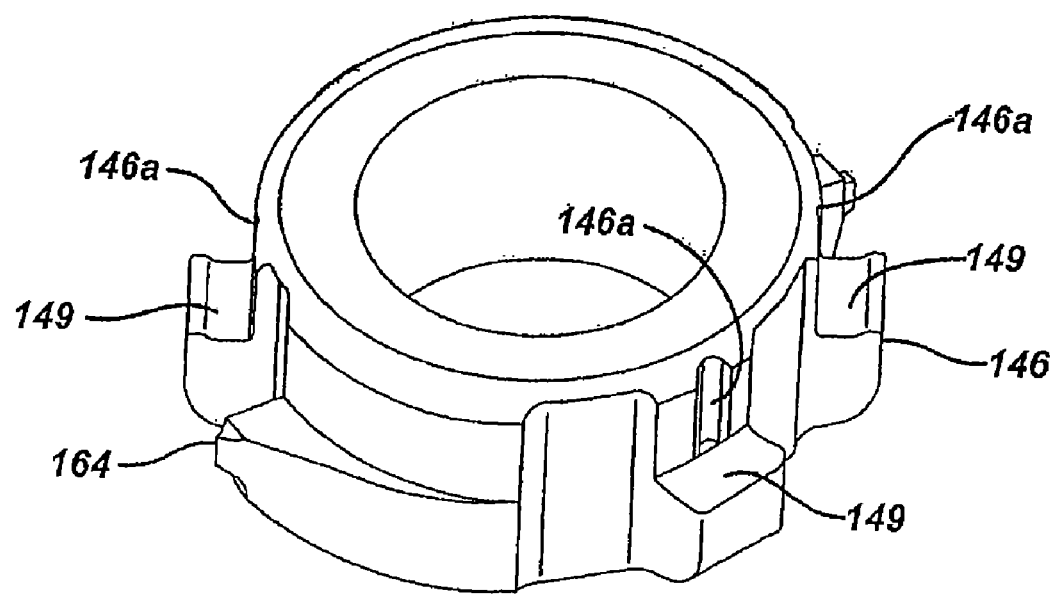
FIGS. 7A, 7B and 7C illustrate cap, head and assembled structure, respectively, of another internal twist cap embodiment.
Figure 7B:
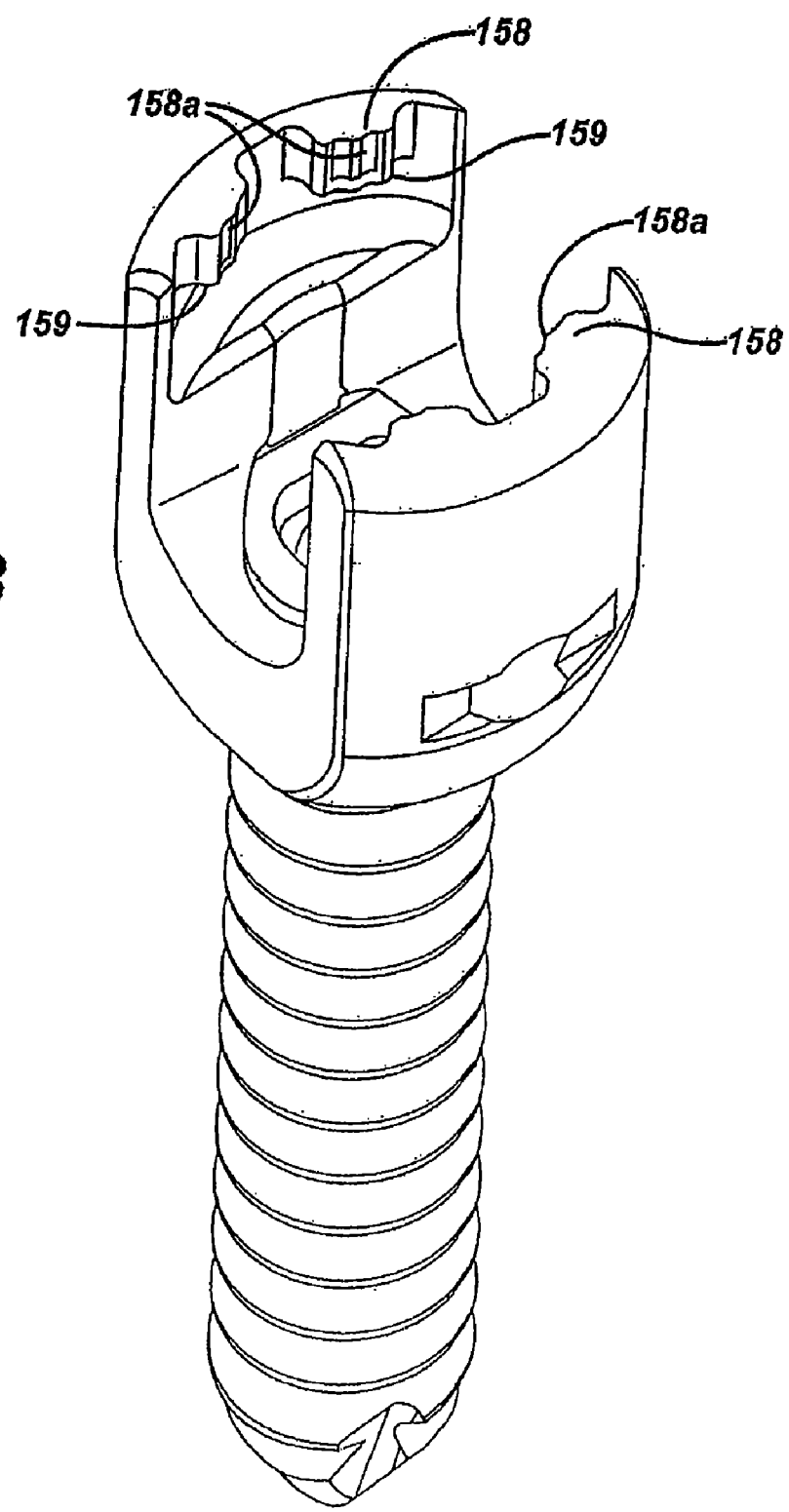
Figure 7C:
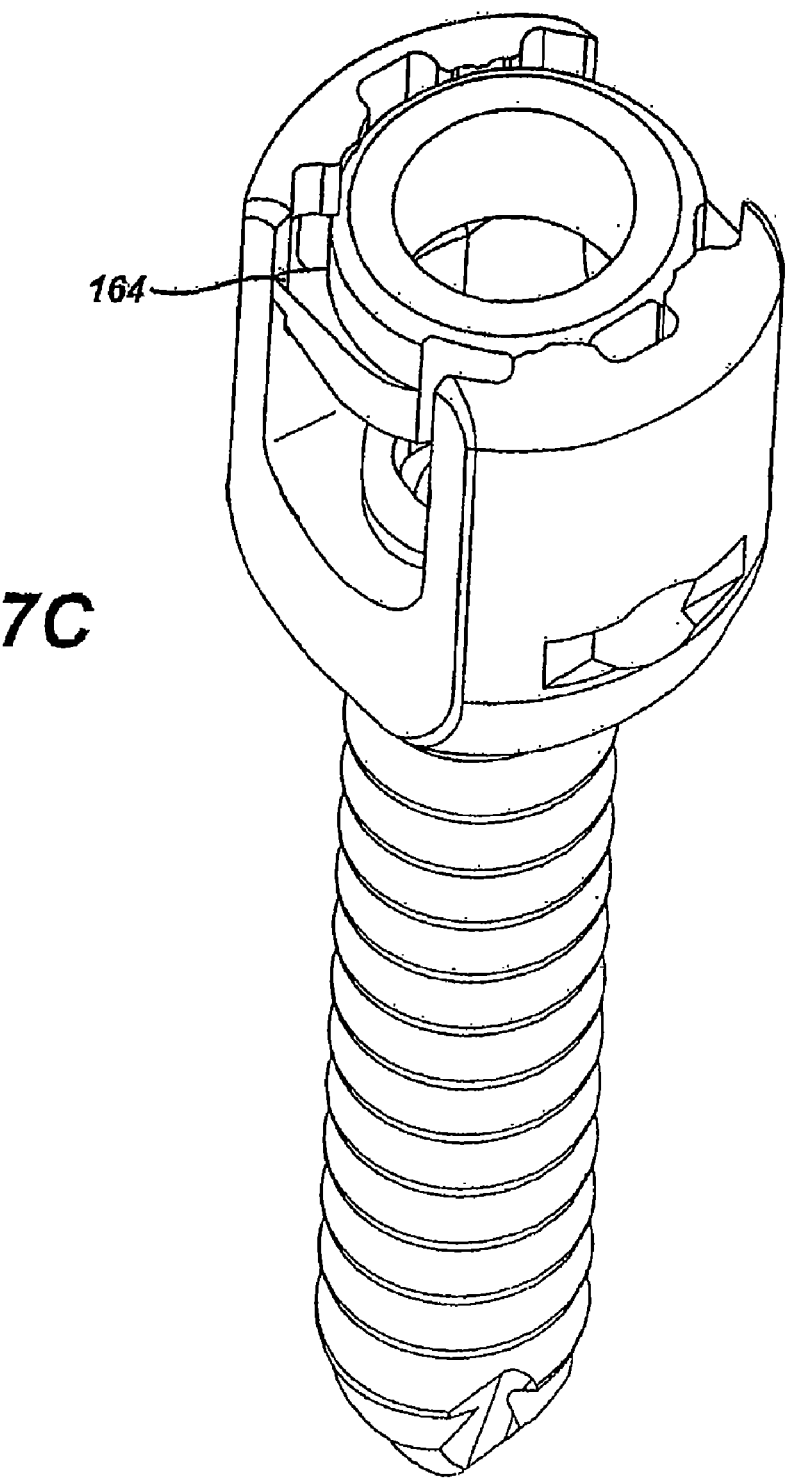

FIGS. 7A–7C illustrate another embodiment of a twist-in closure cap and spinal anchor assembly, having an anchor screw, a slotted head and a twist-in closure cap. As in the previously described embodiments, the screw and head may be separate assemblies, e.g., to achieve freedom in angular orientation before clamping down. The head and cap structure similarly may be adapted to spinal anchor assemblies of other types, such as transverse connectors, anchor plates and other link-receiving hardware. As with the earlier described embodiments, the cap may have a central bore which is internally threaded to accommodate a clamping set screw to lock and immobilize the linkage once it has been captured in the slot; however, to simplify the drawing, threads are omitted from FIGS. 7A and 7C.

In this embodiment, the radially protruding bosses or flange segments 146 of the cap, and the inwardly protruding bosses 158 of the head are arranged so the respective inward and outward directed segments pass between each other, when the cap is pushed downwardly into the head, in a manner similar to the above-described embodiments. Thus, the segments 146 fit between corresponding, inwardly protruding segments 158 of the head and lock thereagainst by a small rotation of the cap. In addition, the twist-lock mechanism may be configured to exert enhanced contact force in a detent region when the clamp screw is tightened down.

As shown in FIGS. 7A–C, this is achieved in a presently preferred embodiment by providing lower and upper contact faces 159, 149 on the segments 158, 146 of the head and cap, respectively, that slope downward toward the center so that when the set screw is tightened the upward force on the cap draws the segments 158 inward and upward. A vertically-oriented protruding ridge 158*a* and mating groove 146*a* are formed on the head and cap, on or directly above the corresponding flange region of each, so that the ridge 158*a* on the head is urged inwardly against the groove surface of the cap. This effectively locks the rotational detent to prevent any rotational movement of the cap once the set screw is tightened.

As further seen in FIGS. 7A and 7C, the twist-in cap has a protruding stop face 164 that contacts the head and prevents over-rotation of the cap when it is turned to close the head. Thus, upon insertion the cap rotates (clockwise as shown) to position the bosses 146, 158 exactly opposite each other as the anchor assembly is closed. The set screw is then tightened to secure the fixation linkage captured in the slot.

Further features and advantages of the invention will now be described with respect to a spinal anchor assembly 210 for securing a spinal fixation element 212 illustrated in FIGS. 8A to 8D. Spinal anchor assembly 210, best illustrated in perspective in FIG. 8A and in cross-section in FIG. 8B, includes an anchor element 214 adapted for attachment to bone. Anchor element 214 has a distal portion 216, a proximal portion 218, and an open slot 220 that opens proximally to receive spinal fixation element 212, which, in this embodiment, is a spinal fixation rod. First and second sidewalls 222 and 224 are located on opposite sides of, and serve to define, open slot 220. In its distal portion 218, anchor element 214 includes a hollow cavity 226 configured to receive the head of a polyaxial screw. As described above, a person of ordinary skill in the art will recognize that other bone engaging configurations, such as monoaxial screws or offset bone engaging elements, could be used within the spirit of the invention. Anchor element 214 also defines a central longitudinal axis 228 that is generally perpendicular to spinal fixation element 212 and can include tool engagement elements 236.

A closure element 230 is also provided in open slot 220 to capture and apply pressure to spinal fixation element 212 within the slot. To engage closure element 230, anchor element 214 includes a plurality of anchor flange segments 232 located on proximal portion 218 and extending inward toward longitudinal axis 228. In the illustrated embodiment, there are two anchor flange segments 232, one each extending inward from first and second sidewalls 222, 224. Anchor flange segments 232 each include an inferior contact surface 234 extending in a direction toward the central longitudinal axis and toward distal portion 216 to define a radial slant ("RS" as illustrated in FIGS. 4B, 5, 6B, and 9).

Figure 8A:
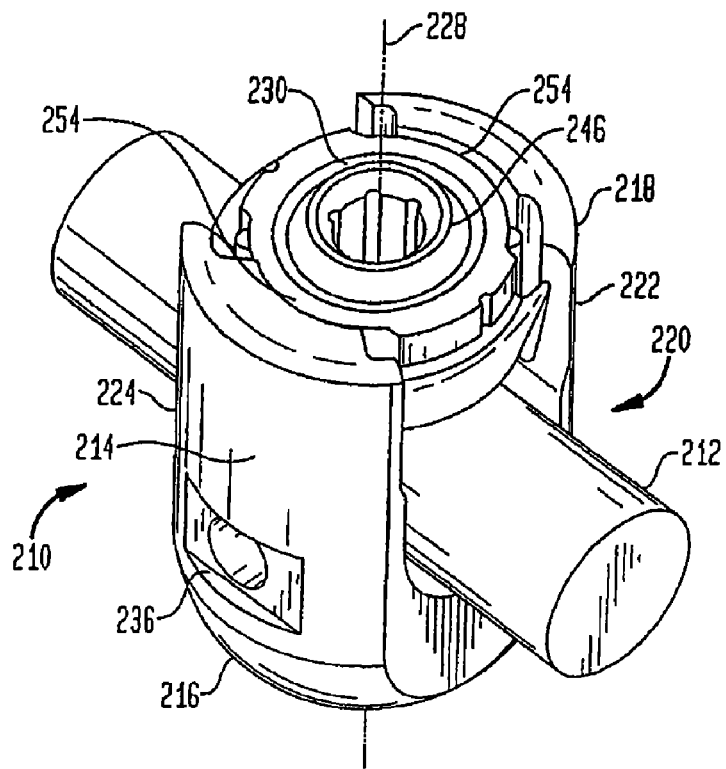
FIGS. 8A and 8B illustrate a illustrates a further spinal anchor assembly of the invention in perspective with an internal twist cap in an open position (8A) and in cross-section with the internal twist cap in a closed position (8B)
Figure 8B:
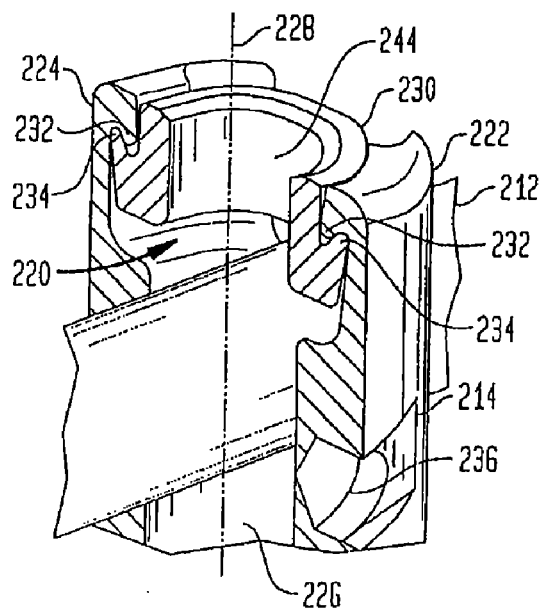
Figure 8C:
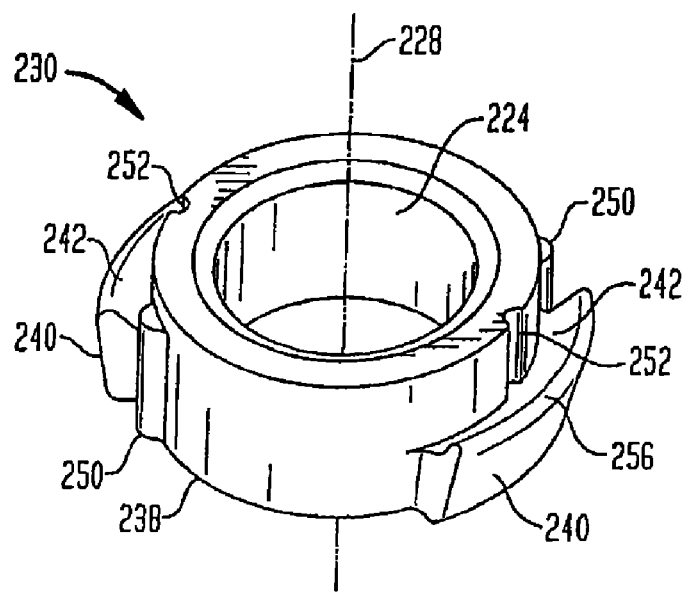
FIGS. 8C and 8D illustrate the twist in cap of FIGS. 8A and 8B in perspective and top view.
Figure 8D:
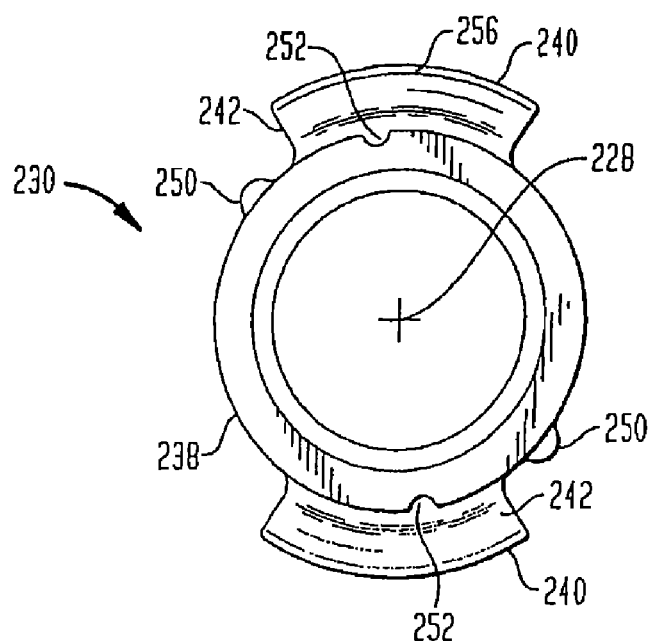

Closure element 230 is further illustrated in FIGS. 8C and 8D, which can be viewed in conjunction with FIGS. 8A and 8B and which show closure element 230 in the context of spinal anchor assembly 210. Closure element 230 includes a closure body 238 and a plurality of closure flange segments 240 extending from closure body 238 in a direction that is transverse to anchor element central longitudinal axis 228 when closure element 230 is placed in the open slot 220. Each closure flange segment 240 includes a superior contact surface 242 extending in a direction away from central longitudinal axis 228 and toward the proximal portion 218 of anchor element 214 at the radial slant (RS) when the closure element is placed in open slot 220 so that closure flange segment superior surfaces 242 engage anchor element flange segment inferior surfaces 234 over a contact area when the closure element is placed in a closed position (as in FIG. 8B) in the anchor element open slot 220.

Closure element 230 can also include a threaded inner surface 244 into which a set screw 246 can be threaded. Thus, in this illustrated embodiment, pressure can be applied to spinal fixation element 212 by first placing closure element 230 in open slot 220 above the spinal fixation element in the open position (FIG. 8A), twisting the closure element so that flange 232, 242 engage (FIG. 8B), and tightening set screw 246 down onto the spinal fixation element to hold it firmly in place.

Closure element 230 can further include one or more tool engagement elements 250 that can be used by an inserter tool to hold and/or twist the closure element into place. Closure element 230 can still further include a locking or detent element 252, in the illustrated embodiment a vertical slot, for engaging a corresponding detent element 254 on anchor element 214. These locking elements are similar to elements 146a and 156a which are more clearly disclosed in FIGS. 7A and 7B. Just as closure detent elements 252 are provided one each per flange segment 240 and are located above the flange, anchor locking elements 254 (vertical protrusions that fit into vertical slots 252) are correspondingly located on anchor flange segments 232 above inferior surface 234. In this way, when closure element 230 is moved from the open to the closed position and sidewalls 222, 224 are provided with some resiliency, anchor detent elements 254 snap into closure detent elements 252 when the closure element reaches the fully closed position to lock the closure element in the closed position.

Figure 9:
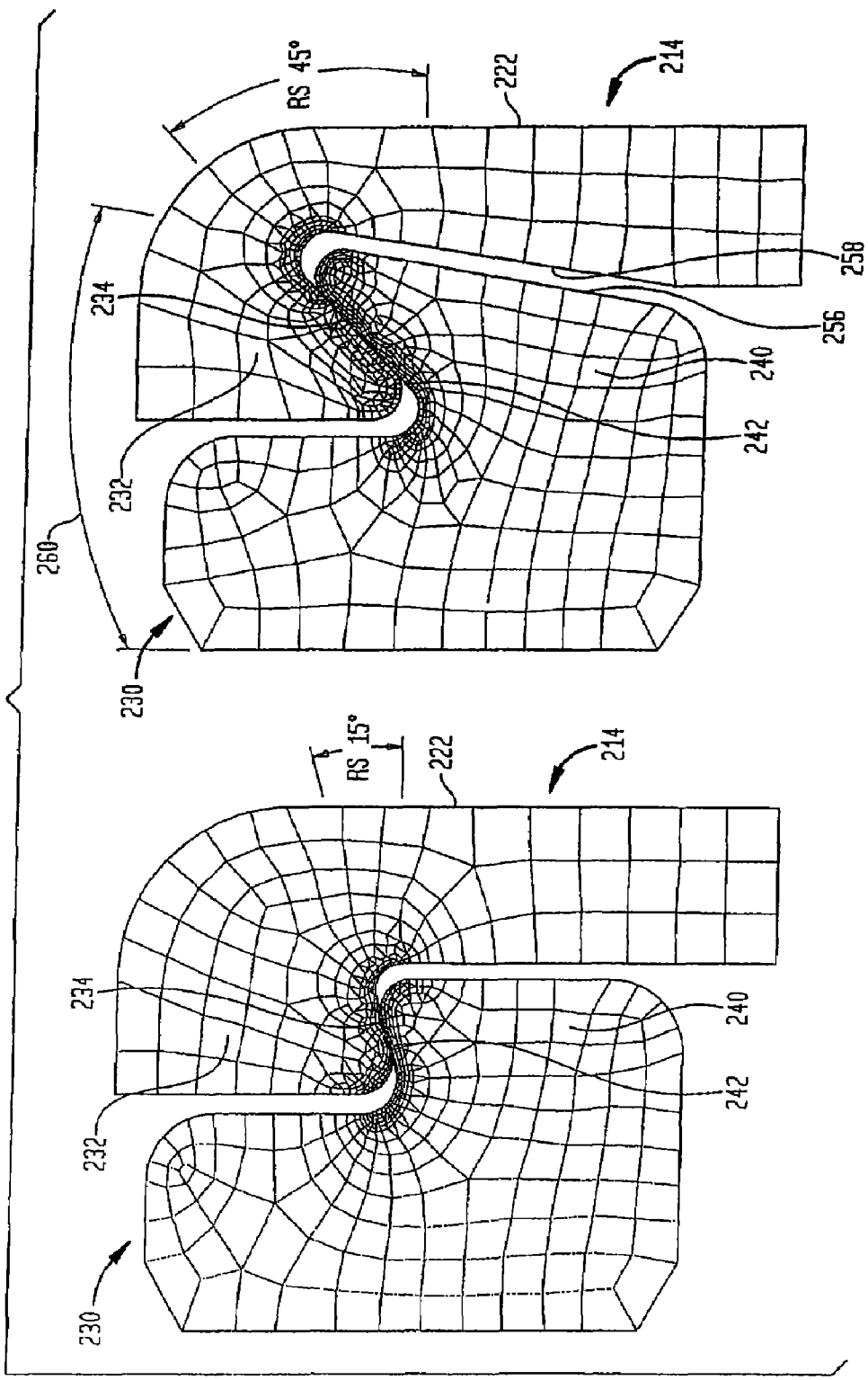
FIG. 9 illustrates in cross-section twist in cap and anchor head combinations of the invention in two different configurations.
Figure 10:
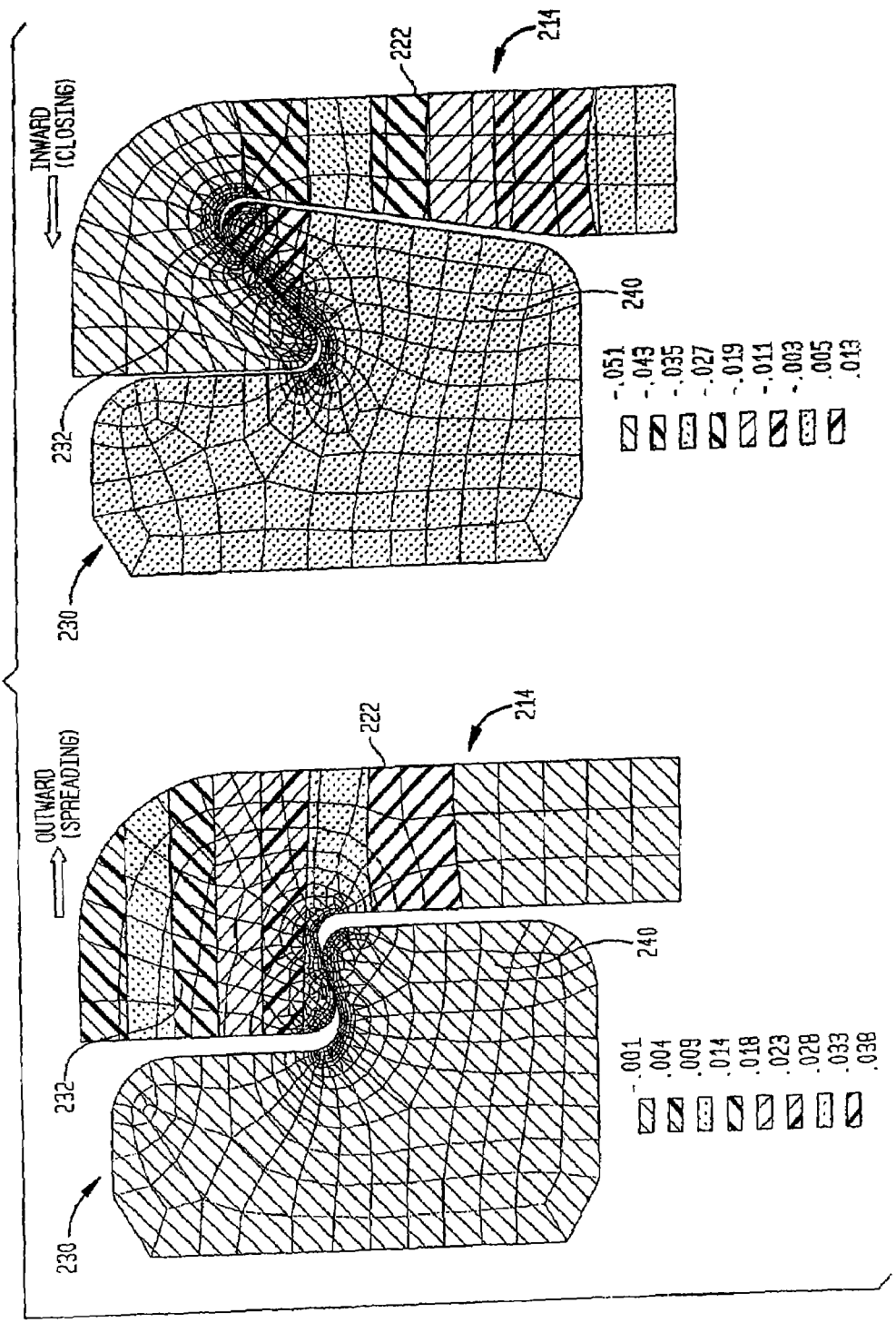
FIG. 10 illustrates the two configurations illustrated in FIG. 9 with a loading applied to show the differing displacement characteristics of the two configurations.

FIGS. 9 and 10 each illustrate two embodiments of a spinal anchor assembly. In the left hand embodiment of FIGS. 9 and 10, a spinal anchor assembly embodiment having a radial slant (RS) of 15 degrees is illustrated. In FIG. 9, closure element 230 is unloaded (no pressure is applied to a spinal fixation element), while in FIG. 10, the closure element is loaded (pressure is being applied to hold a spinal fixation element) and displacement of the features of the spinal anchor assembly is indicated. In the right hand embodiment of FIGS. 9 and 10, a spinal anchor assembly having a radial slant (RS) of 45 degrees is illustrated as well as certain other features of the invention. As with the left hand embodiment, in FIG. 9, closure element 230 is unloaded (no pressure is applied to a spinal fixation element), while in FIG. 10, the closure element is loaded (pressure is being applied to hold a spinal fixation element) and displacement of the features is indicated.

In the right hand embodiment (and as best seen in FIG. 9), an outer surface 256 of closure flange 240 is angled outward (away from central longitudinal axis 228 and toward the proximal portion of anchor element 214) at an angle 260 of approximately 10 degrees. Where outer surface 256 is also curved in a plane transverse to central longitudinal axis 228 (see FIGS. 8C and 8D), outer surface 256 is in the shape of a partial cone as best illustrated in FIG. 8C. Side wall 224 includes a correspondingly angled inner surface 258, allowing cone shaped flange 240 to penetrate into anchor 214 upon closing of closure element 230. In addition, the angled nature of surfaces 256 and 258 allow more mass to be included in closure flange 240, making it stronger and more dimensionally stable, while the removal of mass or thinning of sidewall 222 allows for more resilience, and thus more displacement when such displacement is desired close to flange 232 inward while maintaining strength in lower parts of the sidewall.

The increase in angle from 15 to 45 degrees from the left hand embodiment to the right hand embodiment has a number of implications for an anchor assembly of the invention. One implication is that, since the contact area where flange surfaces 234, 242 meet is increased (and it is also increased as a result of cone angle 260), the stresses at the surfaces are reduced. A further implication is that forces tending to draw sidewall inward will be increased due to the fact that the pressure in the contact area has been "aimed" inward, that is, cos(RS) is larger. In addition, the configuration on the right hand embodiment with RS=45 degrees is such that, when the flanges are loaded (by applying pressure to the spinal fixation element through closure element 230) and sidewall 222 is drawn inward, friction between surfaces 234 and 242 is overcome, allowing the flanges to slide with respect to each other and resulting in sidewall 222 and anchor flange 232 being displaced inward as illustrated in FIG. 10. As shown in FIG. 10, where friction forces are overcome and flanges 232, 240 can slide with respect to each other, anchor flange 232 and at least a portion of sidewall 222 is displaced inward, securing closure element 230 within anchor element 214 and causing locking elements 252, 254 (FIGS. 8A–8D) to more securely lock, resulting in a more permanent and secure fixation of the spinal fixation element to the anchor.

Alternatively, as illustrated in the left hand embodiment in FIG. 10, where angle RS is not steep enough, friction forces between the flanges are not overcome and, as a result of the bending moment placed on sidewall 222 by the upward component of the pressure from closure flange 240 on anchor flange 232, anchor flange 232 and a portion of sidewall 222 may actually be displaced outward, which can have a deleterious effect on the locking provided by elements 252, 254.

It should be understood a person skilled in the art that the specific angles used in the embodiments of FIGS. 9 and 10 can be varied within the scope and spirit of the invention. For example, these embodiments are formed (both closure 230 and anchor 214 elements) from Titanium (the coefficient of friction for Titanium on Titanium being approximately 0.15) and for typical loadings applied to spinal fixation elements, and the above testing shows that 15 degrees of radial slant does not allow the friction forces to be overcome while 45 degrees of radial slant does. A person of ordinary skill in the art can determine specific angles of radial slant useful for particular configurations, materials, and loading forces using finite element analysis tools commonly used in the art.

The invention being thus disclosed and illustrative embodiments depicted herein, further variations and modifications of the invention will occur to those skilled in the art. All such variations and modifications are considered to be within the scope of the invention, as defined by the claims appended hereto and equivalents thereof.

What is claimed is:

1. An anchor assembly for securing a fixation element, comprising:
   an anchor element adapted for attachment to bone and defining a central longitudinal axis, the anchor element having an open slot for receiving the fixation element, side walls on opposed sides of the open slot, a proximal portion, a distal portion, and an anchor flange segment extending from each of the side walls in a direction toward the central longitudinal axis, the anchor flange segments each including an inferior contact surface; and
   a closure element for closing the open slot in the anchor element and applying pressure to the fixation element to capture the fixation element within the open slot, the closure element including a closure body and a plurality of closure flange segments extending from the closure body in a direction that is transverse to the anchor element central longitudinal axis when the closure element is placed in the open slot, each closure flange segment including a superior contact surface extending in a direction away from the central longitudinal axis when the closure element is placed in the open slot so that the closure flange segment superior surfaces engage the anchor element flange segment inferior surfaces over a contact area when the closure element is placed in a closed position in the anchor element open slot;
   wherein the closure flange segments further include exterior surfaces that extend outward away from the longitudinal axis and toward the proximal portion of the anchor element at an angle when the closure element is placed in the open slot to provide a partial cone shaped outer surface to the closure flanges.

2. The assembly of claim 1, wherein the side walls become thinner in a proximal direction to correspond to the partial cone shaped outer surfaces of the closure flanges.

3. The assembly of claim 1, wherein the anchor flange segment inferior surfaces extend in a direction toward the central longitudinal axis and toward the distal portion to define a radial slant and the closure flange segment superior surfaces extend in a direction away from the central longitudinal axis and toward the proximal portion of the anchor element at the radial slant when the closure element is placed in the open slot.

4. The assembly of claim 3, wherein the radial slant is configured to permit the sliding of the anchor flange segment inferior surfaces with respect to the closure flange segment superior surfaces upon pressure being applied on the fixation element.

5. The assembly of claim 3, wherein the radial slant is configured so that, when the closure element is in its closed position and pressure is applied to secure the fixation element within the open slot in the anchor element, the sidewalls are drawn together.

6. The assembly of claim 3, wherein the radial slant is at an angle of approximately 45 degrees to the central longitudinal axis.

7. The assembly of claim 1, wherein the closure element and anchor element each include detent elements that engage to lock the closure element in the closed position.

8. The assembly of claim 7, wherein a first one of the closure and anchor detent elements is a protrusion and a second one of the closure and anchor detent elements is a recess configured to capture the protuberance.

9. The assembly of claim 8, wherein the anchor detent element is provided on the anchor flange segment.

10. The assembly of claim 9, wherein the first one of the closure and anchor detent elements is a longitudinal protrusion and the second one of the closure and anchor detent elements is a longitudinal slot.

11. The assembly of claim 9, wherein the flanges are configured such that applying pressure to the fixation element within the slot causes the detent elements to engage with greater strength.

12. The assembly of claim 1, wherein the closure element further includes a centrally placed clamping member for applying pressure to the fixation element within the slot.

13. The assembly of claim 12, wherein the clamping member is a set screw.

14. An anchor assembly for securing a fixation element, comprising:
   an anchor element adapted for attachment to bone and defining a central longitudinal axis, the anchor element having an open slot for receiving the fixation element, side walls on opposed sides of the open slot, a proximal portion, a distal portion, and an anchor flange segment extending from each of the side walls in a direction toward the central longitudinal axis, the anchor flange segments each including an inferior contact surface extending in a direction toward the central longitudinal axis and toward the distal portion to define a radial slant; and a closure element for closing the open slot in the anchor element and applying pressure to the fixation element to capture the fixation element within the open slot, the closure element including a closure body and a plurality of closure flange segments extending from the closure body in a direction that is transverse to the anchor element central longitudinal axis when the closure element is placed in the open slot, each closure flange segment including a superior contact surface extending in a direction away from the central longitudinal axis and toward the proximal portion of the anchor element at the radial slant when the closure element is placed in the open slot so that the closure flange segment superior surfaces engage the anchor element flange segment inferior surfaces over a contact area when the closure element is placed in a closed position in the anchor element open slot;

wherein the radial slant causes sliding of the anchor flange segment inferior surfaces with respect to the closure flange segment superior surfaces upon pressure being applied on the fixation element so that a sidewall of the anchor element and anchor flange segment are displaced inward toward the central longitudinal axis.

15. The assembly of claim 14, wherein the closure flange segments further include exterior surfaces that extend away from the longitudinal axis and proximally when the closure element is placed in the open slot to provide a partial cone shaped outer surface to the closure flanges.

16. The assembly of claim 15, wherein the side walls become thinner in a proximal direction to correspond to the partial cone shaped outer surfaces of the closure flanges.

17. The assembly of claim 14, wherein the radial slant is configured so that, when the closure element is in its closed position and pressure is applied to secure the fixation element within the open slot in the anchor element, the sidewalls are drawn together.

18. The assembly of claim 14, wherein the radial slant is at an angle of approximately 45 degrees to the central longitudinal axis.

19. The assembly of claim 14, wherein the closure element and anchor element each include detent elements that engage to lock the closure element in the closed position.

20. The assembly of claim 19, wherein a first one of the closure and anchor detent elements is a protrusion and a second one of the closure and anchor detent elements is a recess configured to capture the protuberance.

21. The assembly of claim 20, wherein the anchor detent element is provided on the anchor flange segment.

22. The assembly of claim 21, wherein the first one of the closure and anchor detent elements is a longitudinal protrusion and the second one of the closure and anchor detent elements is a longitudinal slot.

23. The assembly of claim 19, wherein the radial slant is in a direction such that applying pressure to the fixation element within the slot causes the detent elements to engage with greater strength.

24. The assembly of claim 14, wherein the closure element further includes a centrally placed clamping member for applying pressure to the fixation element within the slot.

25. The assembly of claim 24, wherein the clamping member is a set screw.

* * * * *